United States Patent
Griffiths et al.

(10) Patent No.: US 6,270,641 B1
(45) Date of Patent: Aug. 7, 2001

(54) METHOD AND APPARATUS FOR REDUCING SAMPLE DISPERSION IN TURNS AND JUNCTIONS OF MICROCHANNEL SYSTEMS

(75) Inventors: Stewart K. Griffiths, Danville; Robert H. Nilson, Cardiff-by-the-Sea, both of CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/299,269

(22) Filed: Apr. 26, 1999

(51) Int. Cl.[7] .................................................. G01N 27/26

(52) U.S. Cl. ........................ 204/451; 204/450; 204/600; 204/601; 422/70; 422/99

(58) Field of Search .............................. 210/656; 204/450, 204/451, 600, 601; 422/50, 70, 81, 129, 99, 100

(56) References Cited

U.S. PATENT DOCUMENTS

| | | | |
|---|---|---|---|
| 4,551,251 | * 11/1985 | Kolobow et al. | 210/635 |
| 4,868,129 | * 9/1989 | Gibbons et al. | 436/179 |
| 5,092,973 | 3/1992 | Zare et al. | 204/452 |
| 5,194,133 | * 3/1993 | Clark et al. | 204/608 |
| 5,429,728 | 7/1995 | Gordon | 204/453 |
| 5,486,335 | 1/1996 | Wilding et al. | 422/55 |
| 5,785,831 | 7/1998 | Bek | 204/451 |
| 5,800,690 | 9/1998 | Chow et al. | 204/451 |
| 5,802,689 | 9/1998 | Sano | 29/33 T |
| 5,814,739 | 9/1998 | Van Cleve | 73/861.357 |
| 5,830,196 | 11/1998 | Hicks | 604/523 |
| 5,833,826 | 11/1998 | Nordman | 204/452 |
| 5,842,787 | 12/1998 | Kopf-Sill et al. | 366/340 |
| 5,852,495 | 12/1998 | Parce | 356/344 |

FOREIGN PATENT DOCUMENTS

| | | |
|---|---|---|
| 0023157 | * 1/1981 | (EP) . |
| WO99/24828 | 5/1999 | (WO) . |
| WO99/35489 | 7/1999 | (WO) . |

OTHER PUBLICATIONS

Culbertson, C.T. et al., "Dispersion sources for Compact Geometries on Microchips", Anal. Chem., 1998, 70, 3781–3789 Sep.

(List continued on next page.)

Primary Examiner—Jill Warden
Assistant Examiner—Alex Noguerola
(74) Attorney, Agent, or Firm—Burns, Doane, Swecker & Mathis, L.L.P.

(57) ABSTRACT

The performance of microchannel devices is improved by providing turns, wyes, tees, and other junctions that produce little dispersions of a sample as it traverses the turn or junction. The reduced dispersion results from contraction and expansion regions that reduce the cross-sectional area over some portion of the turn or junction. By carefully designing the geometries of these regions, sample dispersion in turns and junctions is reduced to levels comparable to the effects of ordinary diffusion. A numerical algorithm was employed to evolve low-dispersion geometries by computing the electric or pressure field within candidate configurations, sample transport through the turn or junction, and the overall effective dispersion. These devices should greatly increase flexibility in the design of microchannel devices by permitting the use of turns and junctions that do not induce large sample dispersion. In particular, the ability to fold electrophoretic and electrochrornatographic separation columns will allow dramatic improvements in the miniaturization of these devices. The low-lispersion devices are particularly suited to electrochromatographic and electrophoretic separations, as well as pressure-driven chromatographic separation. They are further applicable to microfluidic systems employing either electroosrnotic or pressure-driven flows for sample transport, reaction, mixing, dilution or synthesis.

63 Claims, 10 Drawing Sheets

OTHER PUBLICATIONS

Giddings, J.C., "Coiled Columns and Resolution in Gas Chromotography" *J. Chromatog.*, 3 (1969) 520–523; month unknown.

Jacobson, S.C., et al., "Effects of Injection Schemes and Column Geometry on the Performance of Microchip Electrophoresis Devices", *Anal. Chem.* 1994, 66, 1107–1113; Apr.

Kasicka, V. et al., "Contribution of capillary coiling to zone dispersion in capillary zone electrophoresis", *Electrophoresis*, 1995, 16, 2034–2038; month unknown.

Nilson, R.H., et al., "Wormhole Growth in Soluble Porous Materials", *Physical Review Letters*, 1990, V. 65, No. 13, 1583–1586; Sep.

Nilson, RH. et al., "Free Boundary Problem of ECM by Alternating–Field Technique on Inverted Plane", *Computer methods in applied mechanics and engineering* 6 (1975) 265–282. month unknown.

* cited by examiner

US 6,270,641 B1

METHOD AND APPARATUS FOR REDUCING SAMPLE DISPERSION IN TURNS AND JUNCTIONS OF MICROCHANNEL SYSTEMS

This invention was made with Government support under Contract No. DE-AC04-94AL85000 awarded by the U.S. Department of Energy to Sandia Corporation. The Government has certain rights to the invention.

FIELD OF THE INVENTION

Microfiche Appendix

This document includes a microfiche appendix which contains 1 microfiche having a total of 88 frames.

References

The following publications are cited in this application as superscript numbers:

[1] Kopf-Sill, A. R. and J. W. Parce, "Microfluidic Systems Incorporating Varied Channel Dimensions," U.S. Pat. No. 5,842,787 (1998).

[2] Nordman, E. S., "Method and Apparatus for Reducing the Distortion of a Sample Zone Eluting from a Capillary Electrophoresis Capillary," U.S. patent application Ser. No. 5,833,826 (1998).

[3] Culbertson, C. T., Jacobson, S. C., and J. M. Ramsey, "Dispersion Sources for Compact Geometries on Microchips," Analytical Chemistry, 70 (18) 3781–3789 (1998).

[4] Giddings, J. C., "Coiled Columns and Resolution in Gas Chromatography", Journal of Chromatography 3, 520–533 (1960).

[5] Jacobson, S. C., et al., "Effects of Injection Schemes and Column Geometry on the Performance of Microchip Electrophoresis Devices," Analytical Chemistry 66 (7) 1107–1113 (1994).

[6] Kasicka, V., et al., "Contribution of Capillary Coiling to Zone Dispersion in Capillary Zone Electrophoresis," Electrophoresis 16, 2034–2038 (1995).

[7] Nilson, R. H. and S. K. Griffiths, "Wormhole Growth in Soluble Porous Materials," Physical Review Letters, 65, 1583–1586 (1990).

[8] Nilson, R. H. and Y. G. Tseui, "Free Boundary Problem of Electrochemical Machining by Alternating Field Technique on Inverted Plane," Journal of Computer Methods in Applied Mathematics and Engineering, 6 (3), 265–282 (1975).

BACKGROUND OF THE INVENTION

Microchannel devices are finding increased use in the separation, identification and synthesis of a wide range of chemical and biological species. Employing transverse channel dimensions in the range from a few microns to about one millimeter, such systems may permit the miniaturization and large-scale integration of many chemical processes in a manner analogous to that already achieved in microelectronics. Applications for microchannel devices now under development include such diverse processes as DNA sequencing, immunochromatography, the identification of explosives, identification of chemical and biological warfare agents, and the synthesis of chemicals and drugs.

In addition to the potential for large-scale integration, the small physical scales of microchannel devices offer a few inherent advantages over their traditional macro-scale counterparts. Traditional chromatographic separations are usually performed in packed columns. The role of the packing is to provide a stationary phase having a large specific surface area for the adsorption of chemical species. Since various chemical species have different absorption probabilities and residence times on the stationary phase, they move with different speeds through the column and thus exhibit a range of arrival times at the column exit. Although larger surface areas provide better separation between arrival times, the use of packing materials causes nonuniformity of the fluid motion. This results in hydrodynamic dispersion of the solute bands or peaks used to distinguish the species. The benefit of the packing material is thus partially offset by the detriment of increased dispersion. This compromise can be avoided at the smaller scale of microchannel devices. Since the specific surface area of a tube or channel is inversely proportional to its minimum transverse dimension, microchannel columns may provide the required surface area without any need for a packing.

One promising method of microchannel separation is electrochromatography in which electric fields are used to drive electroosmotic fluid motion. Such fluid motion results from the applied electric field acting on charges in the electric Debye layer adjacent to the tube or channel walls, inducing a shear stress very near the boundary of the interior fluid. Electroosmotic flows offer two important benefits over pressure-driven flows for the small physical dimensions characteristic of microchannel devices. First, fluid speeds in electroosmotic flows are independent of the transverse tube or channel dimension over a wide range of conditions, making this technique extensible to extremely small physical scales. In contrast, pressure-driven flows require a pressure gradient that increases inversely with the square of the minimum transverse dimension to maintain a given fluid speed.

The second, more important advantage of electroosmotic flows is that the profile of the fluid velocity across a tube or channel is essentially flat over a very broad range of conditions. All variations in the axial velocity are confined to a small region adjacent to the tube or channel walls. The thickness of this fluid-dynamic boundary layer is comparable to the thickness of the electric Debye layer. The benefit of this flat velocity profile is that samples may be transported over long ranges with very little hydrodynamic dispersion due to nonuniform fluid speeds. Although dispersion in both electroosmotic and pressure-driven flows grows as the square of the Peclet number, the coefficient of dispersion in an electroosmotic flow may be many orders-of-magnitude smaller than that for the parabolic velocity profile of a pressure-driven flow. In addition, this low coefficient of dispersion permits optimum operation of an electroosmotic flow at very high Peclet numbers. This minimizes the role of ordinary diffusion in electroosmotic flows, thus offering the potential for long-range transport in chromatographic columns with little axial spreading of solute peaks due to either dispersion or diffusion. This is critical to chromatographic processes that identify chemical species by distinguishing the arrival times of closely spaced peaks or bands.

Another promising approach to microscale chemical analysis is electrophoretic separation. Here the carrier fluid may be either moving or nearly stationary, and an applied electric field is used to drive ionic species through a gel or liquid. Separation occurs because the ion speeds depend on the unique charge and mobility of each species. Provided that the applied field is uniform across the tube or channel cross-section, all ions of the same charge and mobility move at the same speed and so progress along the column without any induced dispersion. Such motion is analogous to the flat velocity profile of an electroosmotic flow, and the various species thus again exhibit unique arrival times at the column exit. Like electrochromatographic processes, electrophoretic separations may be severely degraded by diffusion or dispersion. In the latter case, however, dispersion may arise not only from nonuniformity of the carrier fluid speed but may also arise directly from nonuniformity of the electric field across the column cross-section.

Although species motion in both electrophoretic and electroosmotic transport may be relatively free of both diffusive and dispersive spreading in straight tubes or channels having parallel walls, any local variation in the fluid speed or local field strength introduces dramatic skewing of an otherwise flat interface or species band. Such skewing is known to occur in turns because the fluid moving along the outer radius of a turn must travel further than that moving along the inner radius. This difference in path length is compounded by the electric field gradient which is greater along the shorter inner radius, resulting in a greater fluid speed along the shorter path. Thus, an initially flat interface will be severely skewed in passing through a turn. Moreover, because transverse diffusion quickly redistributes solute concentrations across the channel, such skewing is irreversible, and the net effect of transport through any turn or junction is a large and permanent broadening of any solute peak or interface. Although there have been a number of published studies which demonstrate and quantify the dispersive effects of turns [3, 4, 5, 6] there have been few prior attempts to remedy the problem. As a result, separations are generally performed in straight channels that are limited in length by the maximum substrate dimension. This restriction limits the separation between peaks traveling at different speeds and, so, limits the resolution of separation devices.

Beyond separation processes, sample dispersion also plays an important role in the routine transport of a sample through portions of a microchannel system. In many instances, samples are injected into the channel system via a reservoir and then transported to some remote location where the intended process is performed. Sample dispersion in turns and junctions en route to the new location results in smearing of the sample and the eventual arrival of the sample in a progressive manner spanning some extended period of time. For processes such as mixing, dilution and reaction requiring simultaneous arrival of more than one species or arrival of a sample at some prescribed concentration, such dispersion will thus impair the system performance. Likewise, synthesis via chemical reaction may require precise concentrations and the concurrent transport of multiple species side-by-side in a single channel. In such a case, the dispersion induced by a turn or junction may physically separate the reactants by moving one species ahead of or behind the other. Minimizing dispersion in microchannel devices is thus important to system performance even for processes other than species separation and identification.

Two different approaches have been used in previous efforts to minimize the dispersion induced by turns[1] and by contractions at the ends of separation channels.[2] Nordman[2] utilizes focusing electrodes to obtain a more uniform electric field and, hence, a more uniform flow field in the transition between a separation capillary and a detection region. Similar electrodes might also be used to alter the flow field and reduce dispersion in other types of junctions but only at the cost of greatly increased complexity in fabrication and control of required electrodes and circuitry, particularly in large systems having a multitude of turns and junctions. The more passive approach of Kopf-Sill and Parce[1] seeks to reduce dispersion in turns by the use of advantageous channel geometries. In particular, they recommend channels having small aspect ratios such that the channel depths are much greater than their widths. The smaller channel width helps to reduce the difference in transit time along the inner and outer walls of a turn, thereby reducing dispersion. Kopf-Sill and Parce also suggest that dispersion can be reduced by fabrication of turns having a depth along the inner radius that is greater than that along the outer radius, thereby reducing the fluid speed along the inner radius. Although these measures are capable of reducing dispersion, channel aspect ratios near or above unity have a number of advantages, particularly in fabrication and in the introduction of a packing material or pattern of obstacles needed to increase surface area or to increase species selectivity. Moreover, fabrication of the variable depth channels suggested by Kopf-Sill and Parce would substantially increase costs, since most conventional lithographic and etching processes produce channels, channel molds, or embossing tools having a uniform feature depth.

Kopf-Sill and Parce also indicate that dispersion can be reduced by narrowing the channel around a turn, but go on to state that this increases resistance through the channel, lowers throughput, and causes increased current heating and higher pressures. As a result of these perceived problems, they do not pursue this approach but instead describe only deep narrow channels having an aspect ratio less than one.

SUMMARY OF THE INVENTION

The present invention improves the performance of microchannel systems by providing turns, wyes, tees, and other junctions that generate very little dispersion of a chemical or biological sample as it traverses the turn or junction. The reduced dispersion results from turns and junctions having contraction and expansion regions that constrict the cross-section area in a portion of the turn or junction. By carefully designing the geometries of the constricted portion and adjacent contraction and expansion regions, dispersion produced by the improved turns and junctions is reduced by orders of magnitude below that of conventional devices. Embodiments of the invention include: 45, 90 and 180 degree turns, wyes, and tees, as well as sample splitting devices and serpentine channels for folding long columns into small areas.

In one embodiment, the improved turns and junctions have rectangular cross sections and a uniform depth, permitting straightforward fabrication by conventional etching, molding and embossing techniques. Further, because the turns and junctions are only moderately constricted over relatively short distances, they do not lead to excessive increases in electrical resistance and Joule heating. This is made possible by the use of numerical algorithms to discern turn and junction geometries that dramatically reduce dispersion by contraction and expansion regions that offset most of the dispersion that would otherwise occur.

This invention is applicable to pressure-driven chromatographic separations, electrochromatographic separations and electrophoretic separations, as well as many microfluidic processes such as routine sample transport, sample mixing, sample reaction and species synthesis. It is also applicable to channels and junctions that are open, filled with a gel, or filled with a porous or granular material.

DETAILED DESCRIPTION OF THE INVENTION

I. General

The present invention is directed to improved microchannel devices, systems and methods of using same, which incorporate low-dispersion turns, wyes, tees, and other junctions. These improved devices are applicable to both electrochromatographic and electrophoretic separations, as well as pressure-driven chromatographic separation. They are further applicable to microfluidic systems employing either electroosmotic or pressure-driven flows for sample transport, mixing, reaction, or synthesis. The present invention is applicable to all channel depths and to a range of channel cross sections including, for example, rectangular, trapezoidal and triangular. The present invention also does not require variable channel depth either along or across the channel.

Figure 18A:
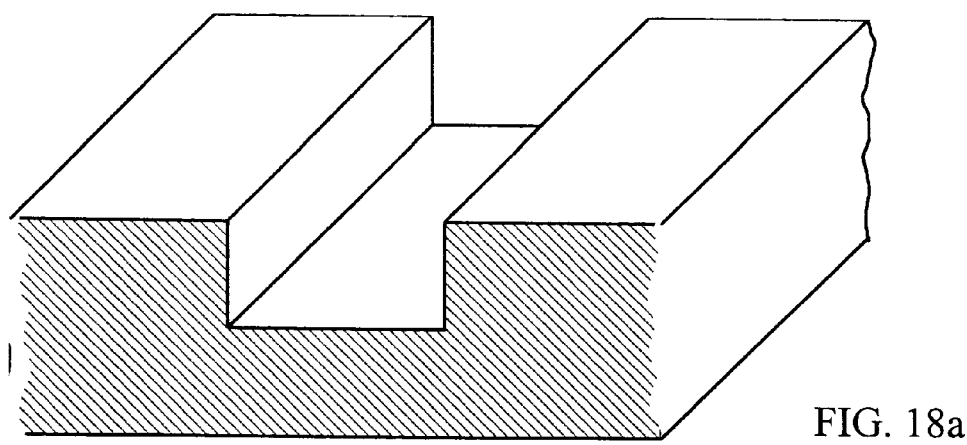
FIGS. 18a, 18b and 18c are cross-sectional views of rectangular, trapezoidal, and triangular channels.
Figure 18B:
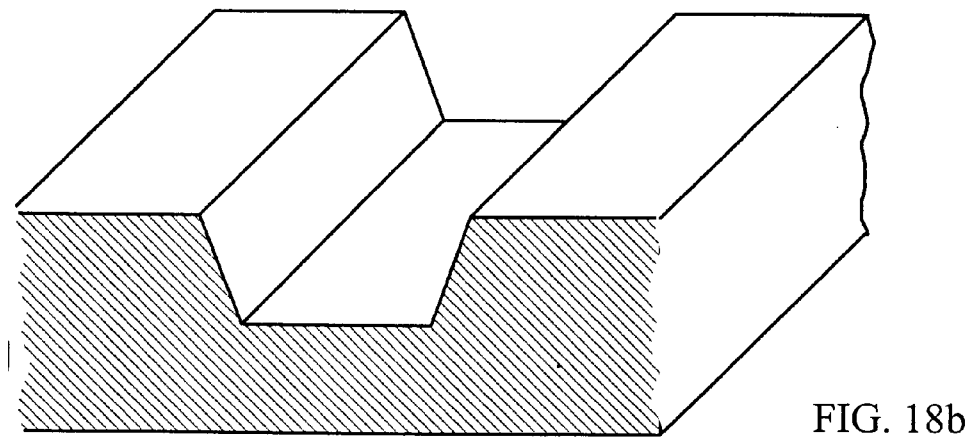
Figure 18C:
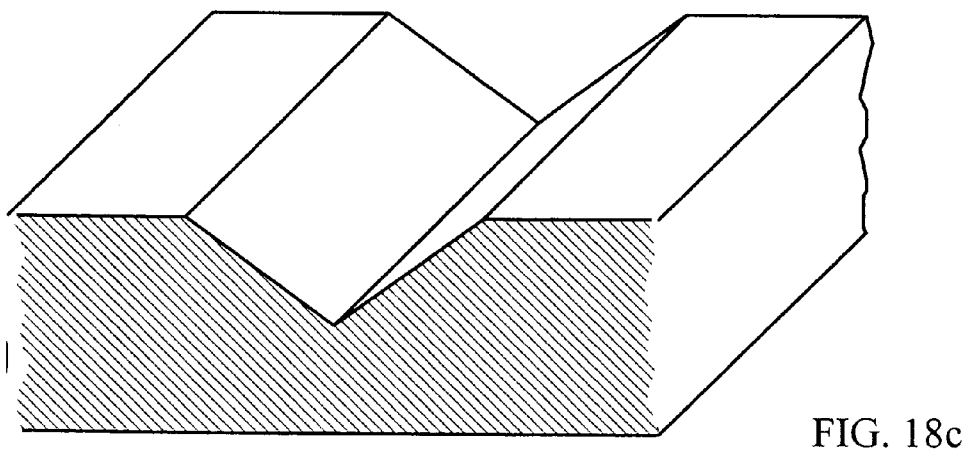

Cross-sectional views of rectangular, trapezoidal, and triangular channels are illustrated in FIGS. 18a, 18b and 18c, respectively.

Microchannel systems typically include multiple transport channels interconnected with one another and with one or more fluid reservoirs. Such systems may be very simple, including only one or two channels, or may be quite complex, including a great many channels and reservoirs. Here we use the term microchannel system to mean any system having one or more channels. When such systems include fluid reservoirs, the reservoirs can serve both as a means for introducing chemical samples into the system and as a convenient location for electrodes connected to an electric controller. This controller is used to apply electric potentials that induce electroosmotic or electrophoretic transport along the channels. Since the transport speed of differing species depends on their adsorption characteristics and relative ratios of ion charge to mobility, microchannel devices are commonly used to perform chemical or biological separation processes. The arrival of separated species peaks or bands is monitored at channel outlets, usually by optical detectors. The timing and intensity of the detector response is then used to infer the composition of the sample under analysis.

Microchannels generally have at least one internal transverse dimension that is less than about 1 mm, typically ranging from about 0.1 $\mu$m to 500 $\mu$m. Axial dimensions of these microchannels may reach to 10 cm or more. A network of channels and reservoirs is fabricated on a planar substrate by etching, injection molding, embossing or stamping. Lithographic and chemical etching processes developed by the microelectronics industry are now used routinely to fabricate microchannel systems on silicon and glass substrates having lateral dimensions ranging up to tens of centimeters. Similar etching processes are also used to fabricate microchannel devices on polymeric substrates such as polymethylmethacrylate (PMMA), polycarbonate, polytetrafluoroethylene (TEFLON), polyvinylchloride (PVC), and polydimethylsiloxane (PDMS). However, mass production of microchannel devices is more efficiently performed by stamping, embossing or injection molding of polymeric materials using tools or molds that have been produced by lithography and etching or by electroforming. After fabrication of a microchannel network on a planar substrate it is mated with one or more planar sheets that seal channel tops and/or bottoms while providing access holes for fluid injection and extraction ports as well as electrical connections. In most such fabrication processes, the channel geometries are initially imprinted by lithographic masks capable of accurately reproducing detailed channel dimensions defined by digital data sets or by scanning images like those disclosed herein.

Figure 1:
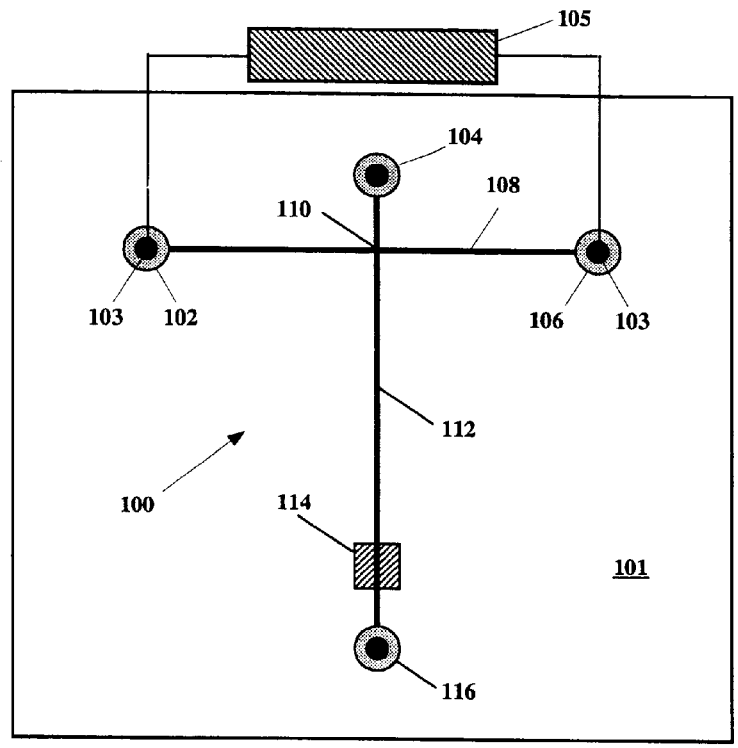
FIG. 1 is a schematic plan view of a microchannel system for performing analyses of chemical and biological samples.

FIG. 1 schematically illustrates a representative chemical analysis system 100 fabricated on a planar substrate 101. The fluid reservoirs 102, 104, 106 and 116 have access ports (not shown) that permit injection or extraction of fluid through the top or bottom faces of the substrate. These ports may also be used to control the hydrostatic pressures in the reservoirs, or they may be left open to maintain reservoir pressures equal to the atmospheric value. Similar access holes are used to insert electrodes 103 that are connected to a controller 105 used to control the electric potentials within the reservoirs. In the system of FIG. 1, a fluid sample is initially injected into reservoir 102 and then transported through channel 108 by raising the electric potential or pressure of reservoir 102 above that in reservoir 106. After completing this step, the separation channel 112 contains a small volume of the sample within the junction 110. The small sample is then moved forward along the separation channel 112 by raising the electric potential or pressure in reservoir 104 above that in 116. Because of differences in surface adsorption, ion charge, and ion mobility, different species within the sample move along the separation channel at different speeds. As a result, the sample separates into a series of bands that are detected as they pass through a detection device 114 located toward the end of the channel. The contents of the sample are inferred from the observed arrival times of the separated bands.

Chemical or biological samples are transported through microfluidic devices by electroosmosis, electrophoresis, or by pressure driven flow. In electroosmosis, bulk flow is induced by applying an electric field to a fluid containing a net mobile charge within the Debye layers adjacent to channel surfaces. In electrophoresis, by contrast, there is generally no bulk motion of the fluid or gel contained within the separation channels. Instead, the applied electric field causes migration of ionic species through a substantially stationary fluid or gel, at speeds that depend on the ion charges and mobilities of the species. Both of these processes may occur simultaneously when an electric field is applied to a fluid, though one is usually dominant. In pressure driven flow, bulk fluid motion is induced by applying a pressure difference between channel ends. The present invention is applicable to all electroosmotic and electrophoretic devices and to pressure driven devices having channel depths small compared to their widths.

To obtain the desired species separation, the separation channel 112 may be filled with a separation matrix such as gel or a porous or granular material. Gels are often employed as the stationary phase in electrophoretic separations. Porous and granular materials are often used in chromatographic separations to increase the surface area and provide a specialized adsorption surface known to selectively retard particular species. Alternatively, the separation matrix used to increase surface area may be a small-scale pattern or array of obstacles fabricated within the channel. The selectivity of these fabricated surfaces may also be altered by coating or chemical processing. Thus, to effectively identify the contents of an unknown sample, it may be transported simultaneously through multiple separation channels having different separation matrices that selectively adsorb different species. Such a system is shown schematically in FIG. 2.

Figure 2:
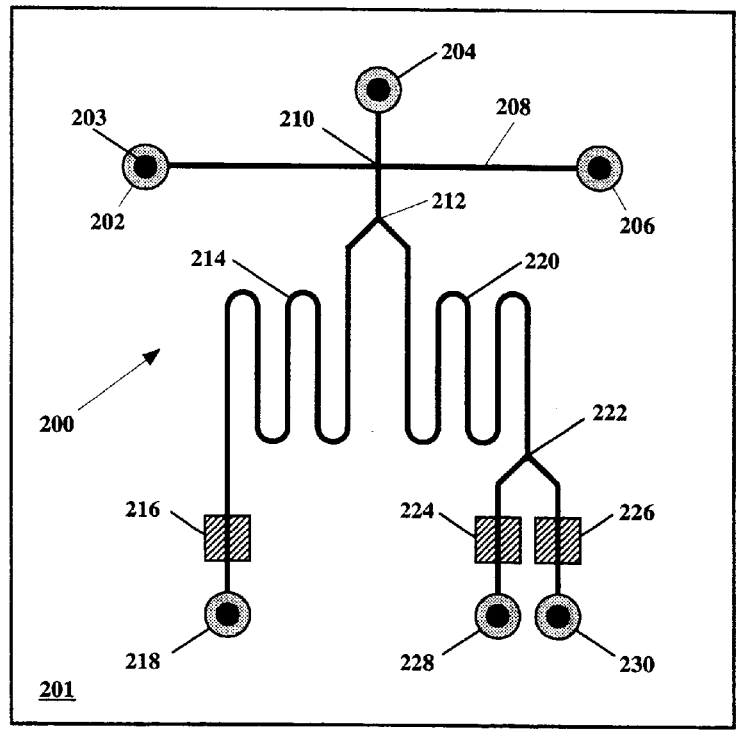
FIG. 2 is a schematic plan view of a microchannel system employing a folded column to increase effective column length and branching junctions to perform parallel processes and parallel detection.

FIG. 2 illustrates a more complex chemical analysis system 200 that includes a pair of folded or serpentine separation channels 214 and 220 fabricated on a planar substrate 201. In analogy to the discussion of FIG. 1, the sample is introduced into reservoir 202 and transported through channel 208 toward reservoir 206. This sample motion is induced by using a controller (not shown) to raise the electric potential of the electrode 203 in reservoir 202 above that in reservoir 206. Alternatively, sample motion may be induced by applying pressures to reservoirs 202 and 206. Then, to move the sample through the system, the electric potential or pressure in reservoir 204 is raised above that in reservoirs 218, 228 and 230. As a result, the volume of sample residing in junction 210 is transported through the branching junction 212 which divides the sample into a pair of sub-samples that are then transported through the separation channels 214 and 220 toward the detectors 216, 224 and 226. Another branching junction 222 is used to divide the sample leaving separation channel 220 into a pair of sub-samples that are sent to separate detectors having differing detection capabilities. Similarly, a confluence junction could be used to route samples coming from multiple separation channels toward a single detector.

The serpentine separation channels 214 and 220 are folded back upon themselves to permit fabrication of long channels on small substrates 201 or within small areas of a larger substrate. Long separation channels are beneficial in producing wider spacing between species bands moving at differing speeds along the channel. However, any dispersion or spreading of species bands reduces the ability to distinguish closely spaced peaks. Thus, effective use of serpentine channels is critically dependent on low-dispersion turning channels, like those disclosed here.

In addition to the separation devices shown in FIGS. 1 and 2, microfluidic devices can also be used to perform a broad range of chemical reaction, mixing, and synthesis processes currently performed at larger scales. Such devices generally involve a large number of transport channels interconnected by numerous junctions. As in separation, many of the chemical processes performed by these devices are degraded by axial dispersion of compositional interfaces. Thus, the broader utility of the present invention is to provide turns and junctions that minimize dispersion and hence enable the design, fabrication, and operation of a broad range of microchannel devices.

II. Mathematical Model

A numerical model describing species transport in electroosmotic flows was developed and used to simulate, quantify and remedy dispersion occurring in microchannel turns and junctions. Although this model is capable of resolving the electric potential and ion concentration gradients within Debye layers, these surface layers are usually orders of magnitude smaller than the transverse channel dimensions. Under these conditions, the governing partial differential equations need only be solved in the electrically neutral core of the flow where the electric potential satisfies the Laplace equation. Once the electric potential is known, its longitudinal gradient can be used to calculate the fluid speed immediately adjacent to the channel walls; the constant of proportionality depends on several parameters such as fluid viscosity and the Debye layer thickness that are independent of position and time. Further, since the fluid flow is incompressible and irrotational within the electrically neutral core, the streamlines of the flow are coincident with the electric flux lines. Such flows, known as potential flows, have been studied extensively in cases where the driving potential is pressure; in the present case, it is the electric field. Consequently, a single solution of the Laplace equation, suitably scaled, depicts both the electric potential and the corresponding flow field for any fixed channel geometry.

The same mathematical model also describes ion motion in electrophoresis through a relatively stationary phase, as well as the bulk fluid motion in some pressure-driven flows. Like electroosmotic fluid speeds, electrophoretic ion speeds are proportional to the gradient of the electric potential. Thus electrophoretic ion motion is completely analogous to fluid motion in electroosmotics. Similarly, the fluid velocity of a pressure-driven flow in a packed channel is proportional to the gradient of the pressure field, which for incompressible fluids also satisfies the Laplace equation. The same equations also describe the depth-averaged speed of pressure-driven flows, often called Hele-Shaw flows, in unpacked channels having a channel depth that is much smaller than the width. In all of these cases, the fluid or species motion obeys the same governing equations as those outlined above for electroosmotic transport. Thus, the dispersion associated with nonuniform fluid speeds across a channel may be calculated in the same manner. Similarly, any remedies to dispersion in electroosmotic flows also serve as remedies to dispersion in electrophoretic processes, Hele-Shaw flows in shallow channels, and pressure-driven flows in packed channels. The Fortran source code for implementing the mathematical model is set forth in the microfiche appendix.

Here the electric field equation was solved by an inverted approach. In this approach, the dependent variables are the unknown values of the spatial coordinates, x and y, and the independent variables are the electric potential, e, and associated stream function, $\psi$. The advantage of this approach is that the computational domain is always rectangular in the e-$\psi$ domain, since the stream function is constant on channel walls and the electric potential or pressure is uniform across straight sections of a channel. The governing equation on the inverted domain is still the Laplace equation. It is easily solved by finite-difference methods in the rectangular e-$\psi$ domain, regardless of the geometric complexity of the channel boundaries in the physical x-y domain. This inverted approach has been previously used to solve free boundary problems in aerodynamics, electrochemical machining [8] and wormhole growth in soluble materials [7].

Figure 3:
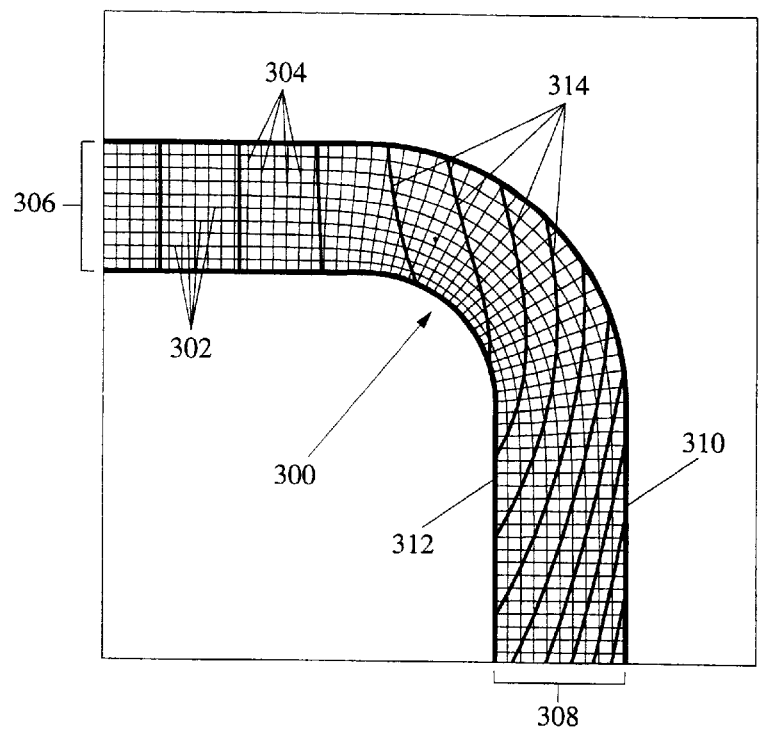
FIG. 3 is a plan view of a standard (prior art) 90 degree turning channel in which sample profiles (heavy lines) remain flat in straight entry section, but are skewed dramatically as sample traverses the turn.
Figure 4:
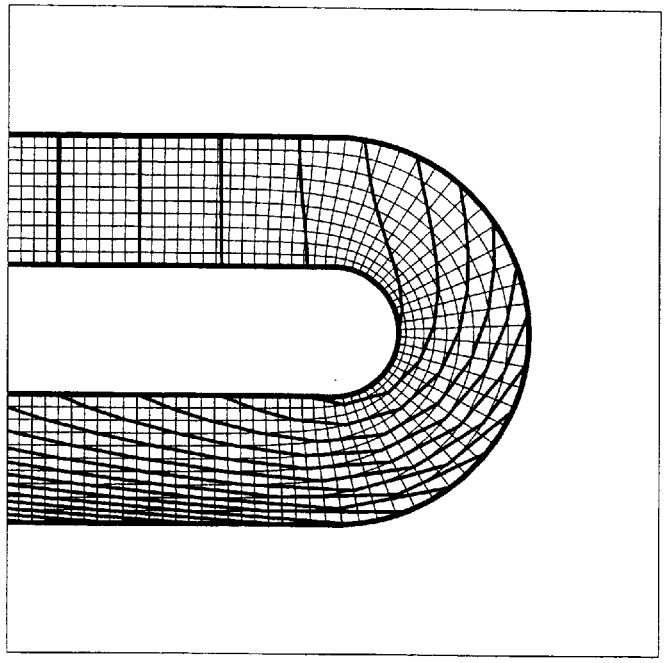
FIG. 4 is a plan view of a standard (prior art) 180 degree turn in which the increased angular extent of this turn increases the skewing of an initially flat sample profile.
Figure 17:
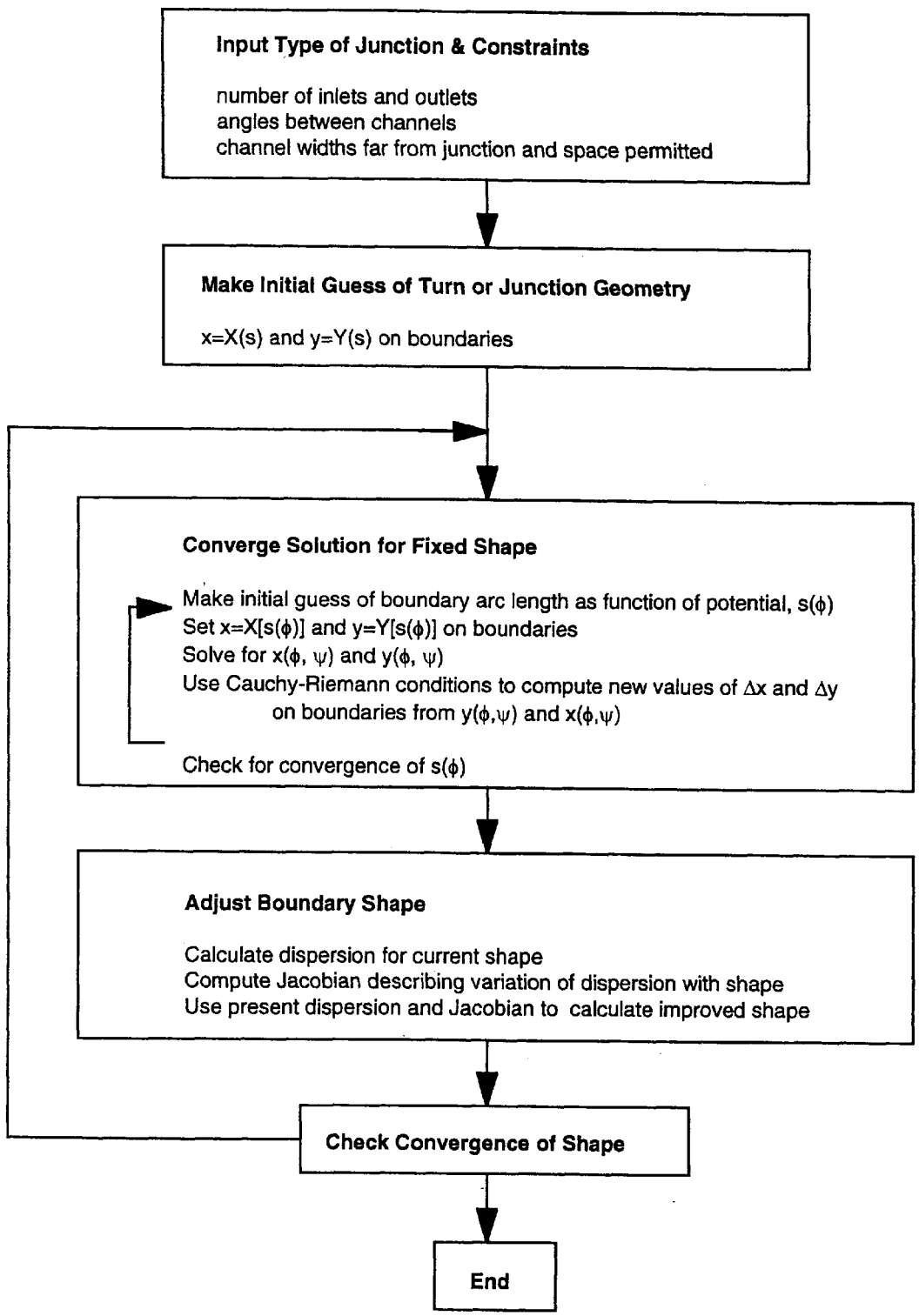
FIG. 17 is a flow diagram of the numerical algorithm used to compute the geometries of low-dispersion turns and junctions.

After obtaining a finite-difference solution to the Laplace equation for a candidate channel shape, local transport speeds, V, are calculated from the potential field gradients at all mesh points. Numerical integration of the function dt=ds/V along each streamline then yields the travel time of Lagrangian tracers simultaneously released from a cross-sectional plane upstream of the turn or junction. These time sequences are then interpolated for chosen values of time to find the simultaneous locations of all tracers. These points are then connected, as shown in FIGS. 3 and 4, to illustrate the distortion of a sample profile as the sample moves through a turn. This computational method has been validated against measured profiles in conventional 90 and 180 degree turns. As explained further below, the mean axial position and standard deviation of the tracer locations servers as a direct measure of dispersion. Given the dispersion for this candidate channel shape, a new channel shape yielding still lower dispersion is discerned and this process is repeated until no further improvement is possible. A flow diagram illustrating the overall numerical procedure is shown in FIG. 17.

The term "low-dispersion" when employed to described the various embodiments of the present invention means that these geometries produce sample dispersion that is one to two orders of magnitude smaller than that produced by conventional turns and junctions. While these low dispersion turns and junctions yield minimum dispersion given the prescribed geometric constraints, it is generally possible to obtain further reductions in dispersion by introducing more freedom in the allowable turn geometry. For example, it will be shown that in general larger radius turns and junctions produce relatively smaller sample dispersion. However, this reduced dispersion comes at the cost of increased substrate area required for the turn or junction and a smaller cross-sectional area of the constriction. The first of these drawbacks undermines one of the principal benefits of the present invention; that is, complex channel networks can be turned or folded to occupy smaller substrate areas. The second of these drawbacks leads to large gradients of the pressure or electric potential within the constriction and the associated problems of excessive driving pressures or of excessive Joule heating and bubble formation via electrolysis.

The low-dispersion shapes computed here are valid for all channel depths, provided that the channel cross-sections are rectangular and the depth is uniform. They are also reasonably valid in describing the top surface or any other horizontal cut through channels that have trapezoidal or triangular cross sections and roughly uniform depth along the channel center, and are further reasonably valid in describing circular or rounded channels provided that the width of these channels is defined as the maximum transverse channel dimension. Similarly, the computed geometries do not depend on the properties of the fluid, the wall potential, or the strength of the electric field, so long as the Debye layer remains thin compared to the transverse channel dimensions. This restriction is satisfied for channel widths greater than about 0.1 $\mu$m, since the Debye layer thickness is typically on the order of 10 to 100 molecular diameters. Indeed, if this restriction were not satisfied, dispersion in straight channels would be unacceptable and as a practical matter the chemistry of the carrier or buffer fluid would be adjusted to reduce the Debye thickness. Thus, the channel shapes presented here may be regarded as universal so long as the width is interpreted as the lateral channel dimension at a fixed vertical elevation.

III. Dispersion Induced by Conventional Turns

Before describing the low-dispersion turns and junctions of the present invention, it is first instructive to review sample dispersion for conventional 90 and 180 degree turns. FIG. 3 illustrates a conventional 90 degree turn 300. As seen on the left side of FIG. 3, the calculated flux lines 302 and isopotential lines (304) are each straight and parallel at the inlet end 306. These meshes become somewhat distorted within the turn, but return to a straight and parallel orientation at the outlet end 308. This local distortion occurs in part because the path length along the outer channel wall 310 is longer than that along the inner channel wall 312. Aside from this difference in path lengths, the closer spacing of the isopotential lines along the inner radius of these turns indicates that fluid or ion speeds are greater along this path. Again, both fluid and ion speeds are everywhere proportional to the electric field strength. FIG. 4 shows similar results for a conventional 180 degree turn.

The heavy lines 314 superposed on FIGS. 3 and 4 illustrate the evolution of a sample profile and dispersion of a single ion species in electrophoretic motion, or of any inert non-diffusing sample carried by an electroosmotic flow, or by some pressure-driven flows. Each sequence of lines shows the time history of an initially flat sample profile injected into the leftmost channel boundary. Since the electric field and fluid velocity are uniform across the entry section, every portion of the sample moves into this region at the same speed. The sample profile therefore remains initially flat and orthogonal to the channel walls as it starts downstream. However, as the sample enters the turn, those portions nearest the inner radius begin to move ahead as a result of greater potential gradient or (equivalently) the greater fluid speed. The outermost portion of the sample eventually requires several times longer to complete the turn fully than does than the innermost portion. Roughly half of this difference in transit times is due to the factor of two difference in path length; the remainder is due to differences in fluid speed and field strength. Once the entire sample has completed the turn, the sample profile propagates downstream without further alteration. Similar results for the 180 degree turn are shown in FIG. 4.

Molecular diffusion is not included in the calculations shown here because it is of secondary importance to the dispersion caused by turns and junctions. The influence of diffusion depends on the Peclet number, Pe=uα/D, which is on the order of 100 for fluid or ion speeds, u=1 mm/s, channel widths, α=100 μm, and diffusion coefficients, D=$10^{-9}$ m²/s, typical of microfluidic systems. Thus the sample will travel about 100 channel widths in the time it takes for diffusion to traverse one channel width. The Peclet number must be this large to prevent severe axial spreading of samples within typical channel runs, even in the absence of turns and junctions. As such, diffusion should not have a significant influence on the scale of a turn. Downstream of a turn, however, transverse diffusion will irreversibly spread a skewed sample profile across the channel to produce a relatively uniform sample slug having a length defined by the leading and trailing edges of the sample profiles shown in FIGS. 3 and 4.

The normalized variance, $L^*=(\sigma/\alpha)^2$, of the sample profile serves as a measure of the dispersion resulting from a turn or other junction that disturbs sample motion. The variance, $\sigma^2$, is calculated in a region of parallel motion several channel widths downstream of the turn or junction. The mean axial position of the sample is first determined from the local sample positions; after this the deviations are computed, squared and summed in the usual fashion. When normalized by the channel width, the variance is proportional to the length, L, of straight channel required to produce a diffusive spreading equal to that due to the turn or junction, $L^*=2L/\alpha/Pe=(\sigma/\alpha)^2$. Thus for a Peclet number of Pe=100 and normalized spreading length of L*=1, the dispersion caused by a junction is the same as that occurring by diffusion alone in a straight run of 50 channel widths (L/α=50).

The 90 and 180 degree turns shown in FIGS. 3 and 4 produce normalized dispersions of L*=0.645 and L*=2.786, respectively. Thus the standard deviation, σ, is roughly doubled by turning through an angle that is twice as large. The dispersion of a turn also depends on the ratio of the outer and inner radii, which are two and three in FIGS. 3 and 4; these are both almost asymptotically large, so have little further affect on dispersion. Although radii ratios near unity are preferred in minimizing dispersion [1], such gradual turns occupy much more space and, for that reason, cannot be used to configure the densely packed channel arrays needed for large-scale integration of microchannel chemical processes. However, if tight turns like that in FIG. 4 are used to fold long channels onto small substrates, the turning dispersion would far exceed that occurring in the straight sections. There is thus a need for turn and junction geometries that produce minimal dispersion, while also conforming to prescribed space limitations.

IV. Low-Dispersion Turns

Figure 5:
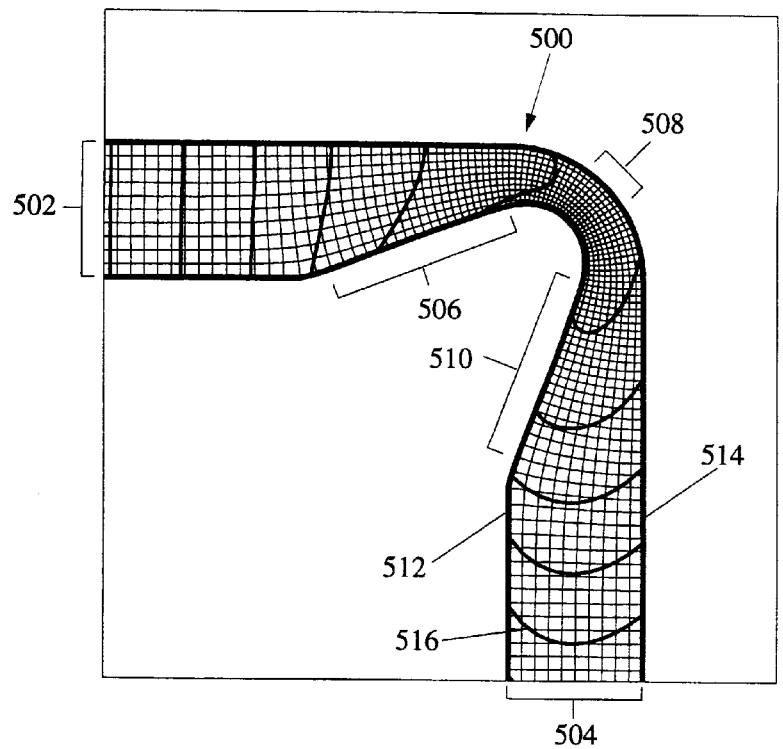
FIG. 5 is a plan view of an improved 90 degree turning channel wherein contraction and expansion regions yield a relatively flat sample profile downstream of the turn.

Dispersion in microchannel turns can be reduced dramatically by the use of engineered geometries, like that shown in FIG. 5. The 90 degree turning channel 500 in FIG. 5 includes inlet and outlet ends 502 and 504 respectively, generally having parallel channel walls, a contraction regions 506 in which the cross-sectional area of the channel is reduced, a constricted region 508 defining the minimum cross-sectional area, and an expansion regions 510 in which the cross-sectional area increases to the original inlet value or to some new channel size. In FIG. 5, the constricted region spans about 30% of the included angle of the turn, defined here as the angle between the main directions of sample motion at the inlet and outlet ends. However, the constricted region may sometimes span nearly 100% of the included angle of the turn, as shown later in FIG. 6. In still other cases, the contraction region may be directly joined to the expansion region such that the angle spanned by the constricted region is essentially zero. Moreover, the direction of sample motion may vary in any of the contraction, constriction and expansion regions of a turning channel. Thus, the sample may be turning even in regions in which the cross-sectional area varies.

Figure 6:
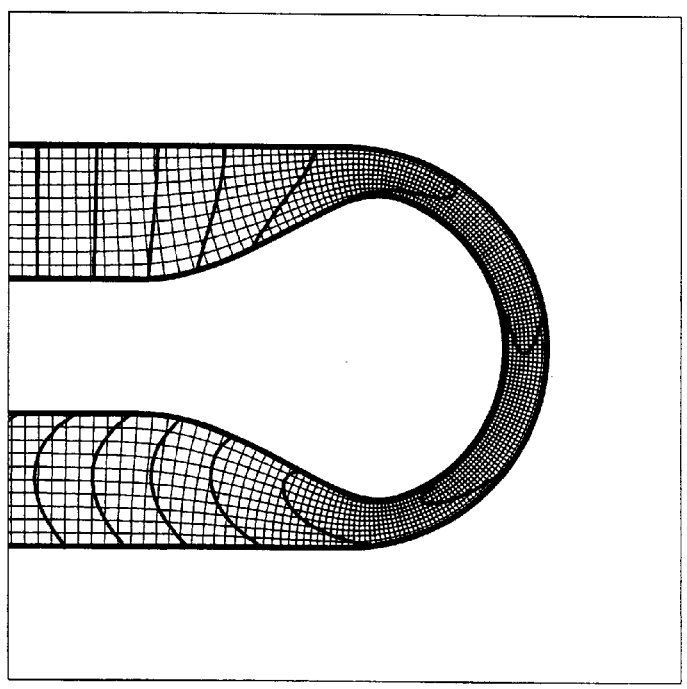
FIG. 6 is a plan view of an improved 180 degree turning channel wherein the width of the constricted portion is about 35% of the widths of the inlet and outlet ends.

The effectiveness of these turning channels is illustrated in FIGS. 5 and 6. For these improved geometries, the 90 and 180 degree turns induce effective dispersions of only L*=0.0057 and 0.0071, two orders of magnitude less than their counterparts in FIGS. 3 and 4. This improved performance is mainly due to three factors. First, the contraction and expansion are formed by reshaping only the inner wall. Thus, for the channels shown in FIGS. 5 and 6, the outer wall of the turning channel consists of linear segments at the inlet and outlet ends joined by an arc of fixed radius spanning the entire included angle of the turn. The outer walls of these low dispersion turns therefore resemble the outer wall of a conventional turning channel. In these cases, only the inner wall of the turning channel is configured to form the contraction and expansion regions of these low-dispersion devices. This increases the path length along the inner channel wall 512 in FIG. 5, making it nearly the same as the outer path length along the outer wall 514 in FIG. 5. Second, the outward movement of the inner wall produces a turn radius ratio much closer to unity. This helps to reduce dispersion occurring within the now constricted turn. Third, the width of the constriction and profiles of the expansion and contraction regions are designed such that the expansion and contraction produce skewing of the sample that just offsets that induced during the turn. This results in a sample profile leaving the turn 516 in FIG. 5, that is slightly bulged but is nonetheless substantially perpendicular to the direction of sample motion.

The turn geometries shown in FIGS. 5 and 6 were designed using a computer program that combines the transport model previously described with a least-squares minimization algorithm. Although this code is fully general in its architecture, the examples presented here are limited to cases having contractions and expansions that mirror one another. The turn geometries shown in FIGS. 5 and 6 are described by three independent parameters: the width of the constriction; the angular span of the constriction; and a value describing the shape of the smooth contraction and expansion before and after the constriction. The solutions have a number of interesting features. The contraction and expansion regions are almost linear, though they are free to exhibit a very wide range of profiles. The contractions and expansions extend just into the turn, though they could have ended either well into or well outside. Finally, the width of the constriction is about 40% of the width of the inlet and outlet ends for the 90 degree case; it is about 30% for the 180 degree turn. These minimum widths provide an ideal balance between the benefit of a radius ratio near unity and the detriment of a very strong contraction and expansion. However, the preferred amount of constriction depends not only on the turning angle but also on the radius of curvature of the turn and the lengths of the contraction and expansion regions relative to the channel width. Thus, the preferred width of the constriction generally varies from about 20% to 80% of the channel width at the inlet end of the turn.

These engineered contractions and expansions are designed to skew the sample profile in a manner that just offsets the sample distortion occurring in the turn. During either contraction or expansion, the longer length and slower speeds along the inclined inner wall tend to retard progress of the sample portion moving along that surface. As seen in FIGS. 5 and 6, the sample profiles thus rotate clockwise as they approach the turn. The turn produces an opposing rotation that is about twice as large, but this is reversed again during the expansion that follows. Sample portions moving along the two opposing channel walls thus reach the exit plane at nearly the same time, but still slightly behind those portions traveling near the channel center.

All contractions and expansions lead to some dispersion of a sample, whether or not a turn or junction occurs within the constriction. This is because sample portions nearest the channel center generally move faster through the expanding and contracting sections and have a shorter path length than those moving along the longer walls. The difference in path lengths and amount of dispersion typically increase with the contraction and expansion area ratios. However, for a given area ratio, the dispersion can always be reduced by more gradual contraction and expansion.

Figure 7:
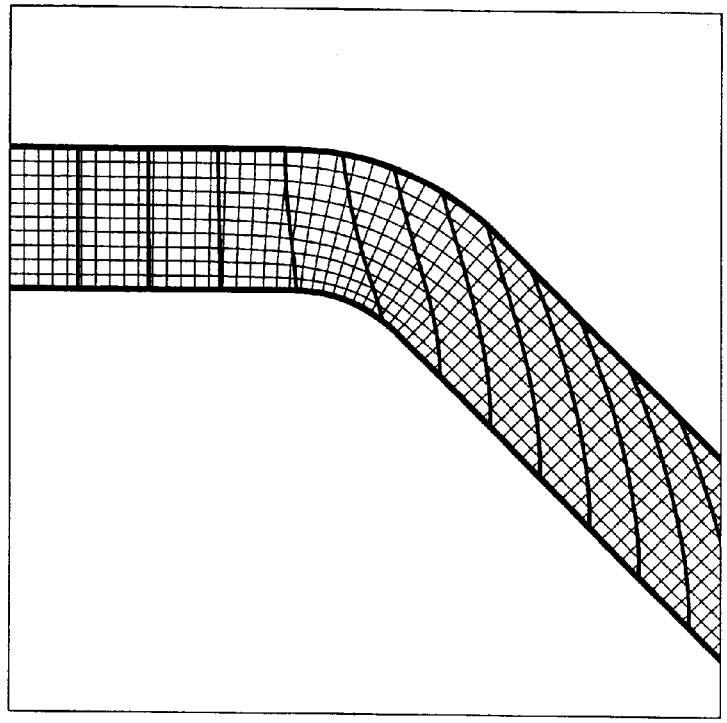
FIG. 7 is a plan view of a standard (prior art) 45 degree turning channel which produces very significant effective dispersion, L*=0.183, even though the included angle of the turn is fairly small.
Figure 8:
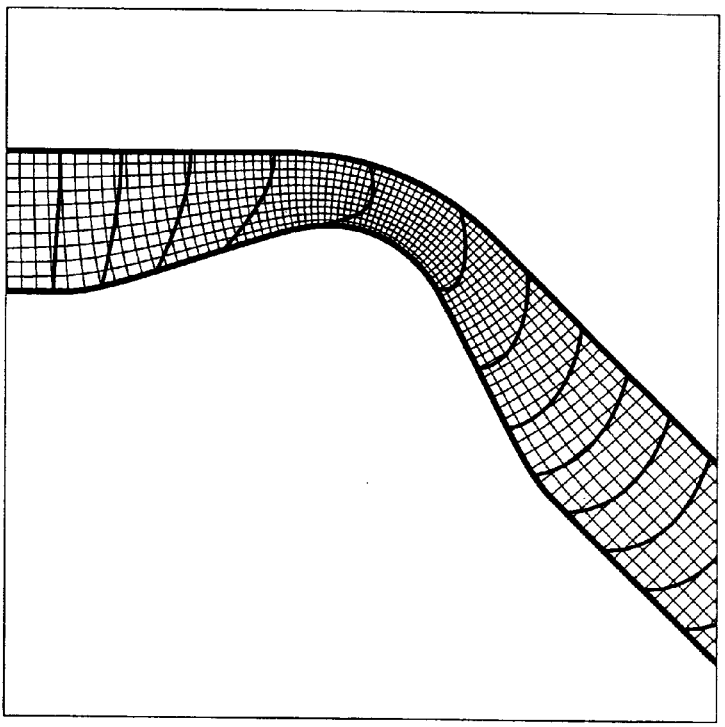
FIG. 8 is a plan view of an improved 45 degree turning channel that reduces the effective dispersion by a factor of about 100 to L*=0.0024.

FIGS. 7 and 8 next illustrate the benefit of a low-dispersion 45 degree turn. In each case the outer radius of the turn is twice the channel width. The first of these shows transport through a standard turn, yielding an effective dispersion of $L^*=0.18$. Despite the relatively small included angle of the turn, this still represents very significant dispersion of the sample. In contrast, the low-dispersion turn shown in FIG. 8 yields a normalized dispersion of only $L^*=0.0024$, nearly a factor of 100 below that of the standard turn. Further, this dramatic improvement in performance is obtained by a constriction in the turning channel that is still 46% as wide as the inlet and exit ends.

Figure 9:
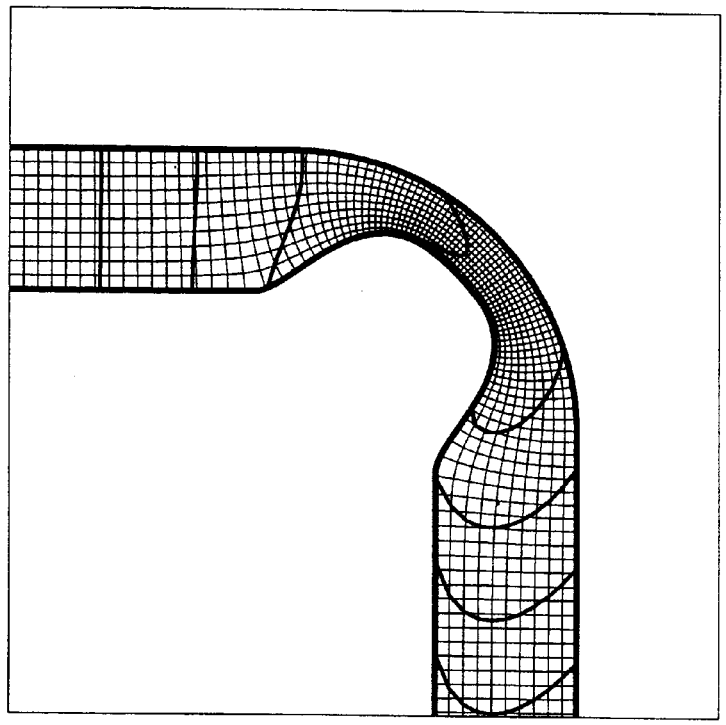
FIG. 9 is a plan view of an improved 90 degree turning channel having abrupt contraction and expansion regions, where abrupt changes in channel width yield a bowed sample profile at the outlet end.
Figure 10:
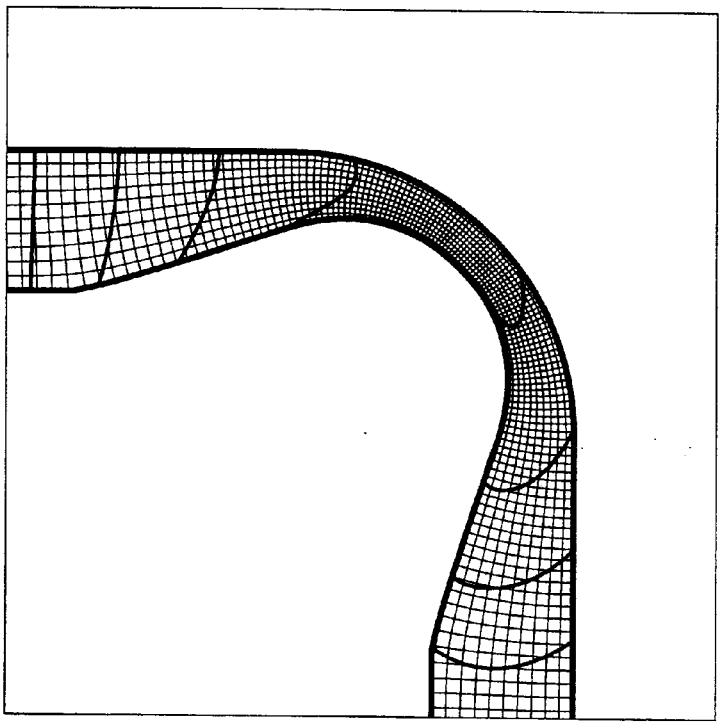
FIG. 10 is a plan view of an improved 90 degree turning channel having gradual contraction and expansion regions that reduce bow of the sample profile at the outlet end.

FIGS. 9 and 10 illustrate the reduction in dispersion achieved by more gradual contraction and expansion. Both of these elbows have an outer radius of two channel widths. Both are low-dispersion geometries, but are subject to differing constraints on the size of the region available for contraction and expansion. In FIG. 9 this region is a square domain of one channel width. The effective dispersion for this case is $L^*=0.011$. However, by increasing the size of the permitted domain to two channel widths, as shown in FIG. 10, the dispersion is reduced by almost a factor of three to $L^*=0.0036$. This reduction is partly due to the more gradual contraction and expansion, but also partly due to a decrease in the ideal width of the constriction for the more gradual contraction and expansion. Although further reductions in dispersion can always be gained by increasing the available space, these benefits come at the cost of reduced feature density within a fixed substrate size.

The preferred lengths of the contraction and expansion regions are determined by practical tradeoffs between reduced dispersion and very narrow channel widths. If the contraction and expansion regions are too short, dispersion may not be reduced to acceptable levels. On the other hand, very long contraction and expansion regions generally yield ideal constrictions of smaller width, leading to possible problems with Joule heating. Thus, the preferred lengths of the contraction and expansion regions usually range from about one to five times the width of the inlet channels. Of course, the contraction and expansion lengths need not be the same, though they are in the specific realizations presented here.

Another method for reducing the inherent dispersion of a contraction and expansion pair is to place streamlined obstacles on the channel centerline either upstream or downstream of the junction. These obstacles increase the path length and reduce the ion or fluid speed well away from the channel walls, reducing the disparity of sample arrival times at the exit plane. A single well-designed obstacle will produce a centerline arrival time nearly coincident with those for paths near the channel walls. The first arrival will then occur at a location midway between the channel center and the wall. Of course it is possible to retard that new first arrival by the placement of additional obstacles, centered on those transverse positions, but the number of obstacles increases and the marginal gains diminish with each new set of obstacles.

V. Low-Dispersion Junctions

In addition to turns, other types of junctions are needed to subdivide samples and join sub-samples together. Here the term junction will be used to describe any device having multiple inlets or multiple outlets or both. Branching junction describes those devices having more outlets than inlets, while confluence junctions have more inlets than outlets. It is clear that branching and confluence junctions may be the same physical device and differ only in the directions of transport through the junction. To describe specific types of junctions, we largely adopt here the familiar terminology of the plumbing industry, wyes, tees and crosses, but all of these are special cases of branching or confluence junctions. The term wye is used here to describe any junction having a single inlet and two outlets as well as any junction having two inlets and a single outlet. The two configurations are interchangeable because the dispersion that occurs is essentially the same regardless of the transport direction. Under these definitions a tee is a special case of a wye having an angle of 90 degrees between the inlet and both outlet ends.

Figure 11:
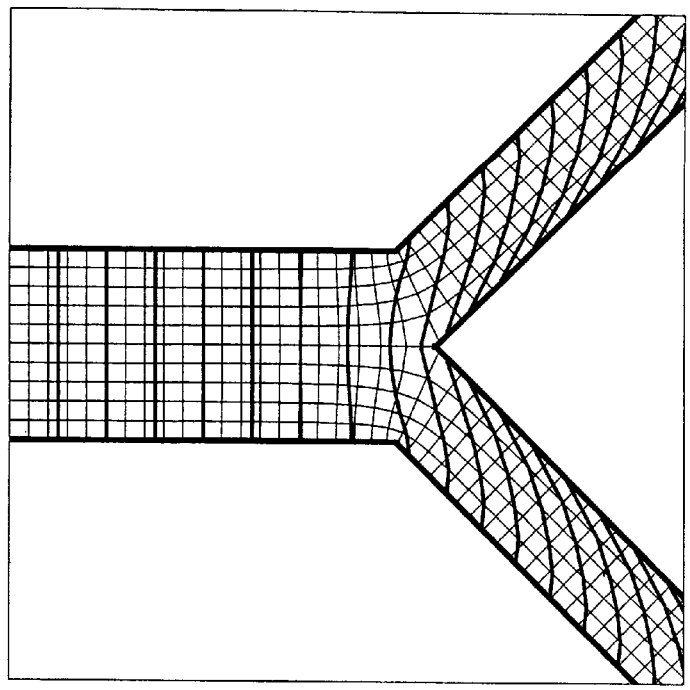
FIG. 11 is a plan view of a standard (prior art) 45 degree wye dividing a sample, where the profile of each subsample is skewed by the junction yielding an effective dispersion of L*=0.183 at the outlet ends.
Figure 12:
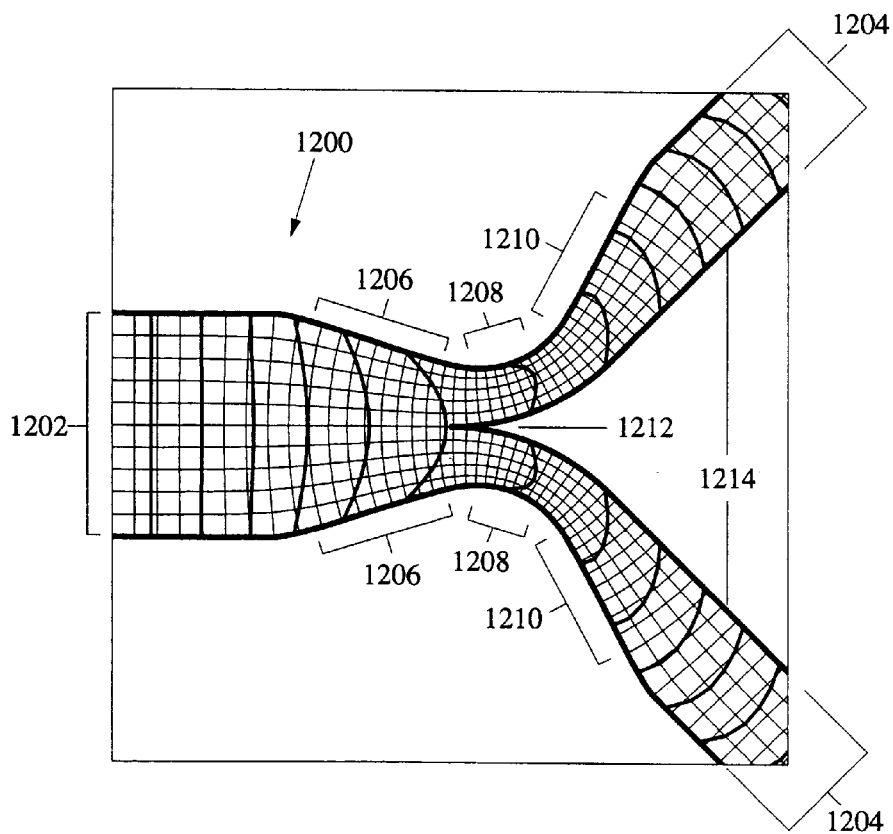
FIG. 12 is a plan view of an improved 45 degree branching junction where contraction and expansion regions reduce the effective dispersion by a factor of about 100 to L*=0.0023.

FIGS. 11 and 12 illustrate the fate of samples split by wye junctions. The standard wye shown in FIG. 11 produces a normalized dispersion of $L^*=0.183$. This is reduced by nearly a factor of 100 to $L^*=0.0023$ by the low-dispersion geometry shown in FIG. 12.

Figure 13:
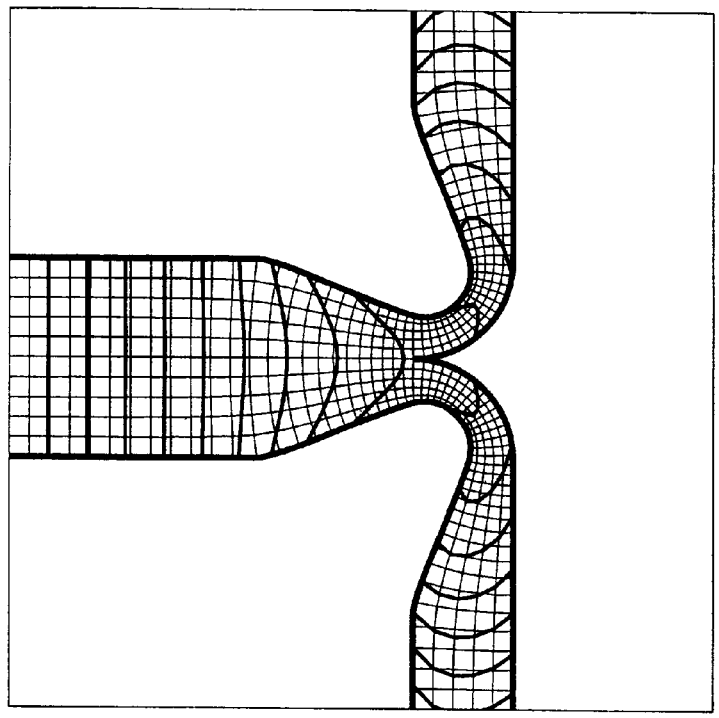
FIG. 13 is a plan view of an improved 90 degree branching junction where contraction and expansion regions and cusplike divider yield an effective dispersion of only L*=0.0055.

As with the turning channels, branching and confluence junctions, including inlet and outlet ends, 1202 and 1204 respectively, are generally defined by parallel channel walls, one or more contraction regions 1206 in which the cross-sectional area of the channel is reduced, one or more constricted portions 1208 defining minimum cross-sectional areas, and one or more expansion regions 1210 in which the cross-sectional area increases. The contraction and expansion regions extend somewhat into the turn, the constriction width is about 40% of the outflow channel width, and the constriction spans about 40% of the included angle of the turn. In addition, the outlet channel walls interior to the junction 1214 meet to form a cusp 1212 facing the inlet end. This cusp divides the sample smoothly without a stagnation zone. As with the turning channels, the geometry shown in FIG. 12 provides nearly equal length of travel along both inner 1214 and outer 1216 channel walls. In the case of the wye, however, the path along the inner wall begins at the center of the inlet end, passes through the cusp, and then follows the interior walls of the two outlet channels. Similar features are apparent in the low-dispersion tee shown in FIG. 13.

The dimensions that characterize preferred junction geometries are essentially the same as those explained earlier for turning channels. The constricted portion of a low-dispersion branching junction should generally have a width that is between 20% and 80% of the width of the outlet ends. Similarly, lengths of the contraction and expansion regions should generally range from about one to five times the width of the inlet. Also as with turning channels, the span of the constricted portion of a branching junction may include nearly all of the included angle or may nearly vanish such that the contraction and expansion regions join almost directly to one another.

Orthogonal cross-junctions or side-branched tees are also needed to inject samples into a main channel containing a carrier fluid or gel. To perform such injection, the sample is usually driven into or across the main channel before applying the pressure or electric field that drives sample motion along the channel. The goal is to inject a narrow, sharply-defined slug for subsequent separation. However, dispersion occurring during and just after injection generally results in a longer, more diffuse sample profile, greatly reducing the ability to distinguish species having similar transit times. The invention described here should prove beneficial in designing sample injection junctions that minimize dispersion. Here again, low-dispersion devices will employ the contraction of channel widths, an injection process at the reduced or constricted scale, followed by expansion back to the final channel width.

Still another means to allow more geometric freedom is to vary the profiles of both the inner and outer radii of the turn or junction. All of the low-dispersion geometries shown thus far have been constructed by altering only the inner wall of the turn. Designs in which both inner and outer walls are displaced have also been examined. The results of these calculations show that dispersion can be reduced somewhat below that for geometries in which only the profile of the inner wall is varied. However, geometries in which both walls are varied generally yield smaller widths of the constricted portion which is generally not desirable. The geometries shown here thus represent preferred embodiments for most applications, but are not intended to indicate that varying both channel walls is not beneficial in some instances.

VI. Serpentine Channels Having Low-Dispersion Turns

Beyond simple elbows, tees and wyes, the present invention enables the construction of pressure-driven chromatographic columns, electrochromatographic columns, and electrophoretic columns that are not straight, but are instead folded back and forth so as to place a much longer effective separation column within the bounds of a fixed substrate area. Current designs, employing only straight separation columns, not only make very poor use of the available substrate area, but also drive manufacturers to large substrate sizes just for the purpose of obtaining sufficient column length. By folding the column, without introducing significant additional dispersion, both of these problems can be solved.

Figure 14:
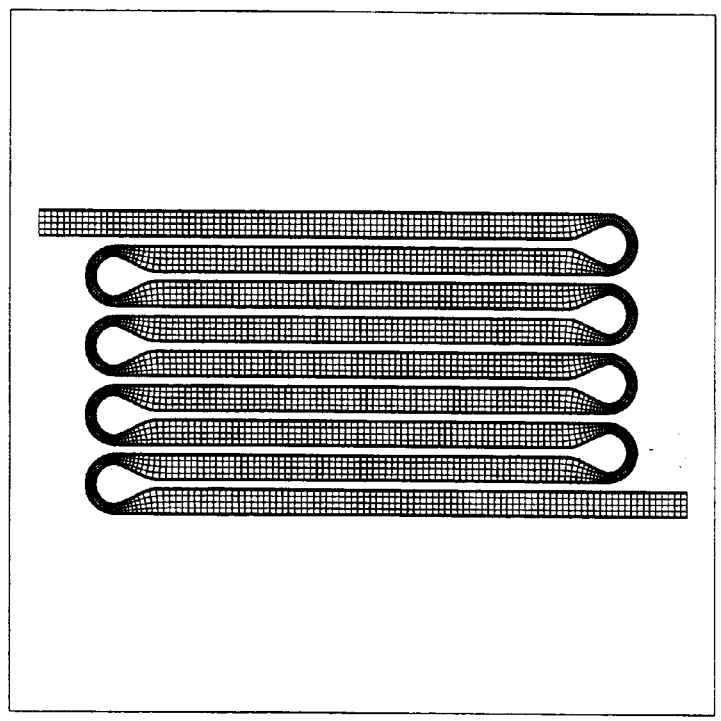
FIG. 14 is a plan view of an improved separation column where the column is folded by low-dispersion turns such that dispersion produced by the turning channels is reduced to levels below that produced by ordinary diffusion in straight sections.

FIG. 14 illustrates one embodiment of the use of low-dispersion turns to fold a long column into a very small space. The turns used in this embodiment yield an effective dispersion of only about 0.0095. For a Peclet number of 100, each turn produces a dispersion equivalent to diffusion occurring in a straight section having a length of only one-half a channel width. Even at a Peclet number of 1000, this equivalent length increases only to about five channel widths. The straight sections in FIG. 14 are roughly 20 channel widths in length. Thus for this range of Peclet numbers, the total induced dispersion of turns will be only 2 to 20% as large as the diffusion in straight sections. This result is independent of the total number of turns and sections since each section is associated with only one turn. Moreover, the turn dispersion relative to diffusion in straight sections decreases as the channel lengths increase. As such, folded columns of arbitrarily long length can be constructed provided that the ratio of the straight section length to the channel width remains larger than about 0.005 times the Peclet number. In contrast, conventional turns would yield a normalized dispersion over 300 times greater than those shown here. For a Peclet number of only 100, such conventional turns would produce a dispersion equivalent to diffusion in a straight section having a length of nearly 160 channel widths.

VII. Structures for Splitting and Joining

Figure 15:
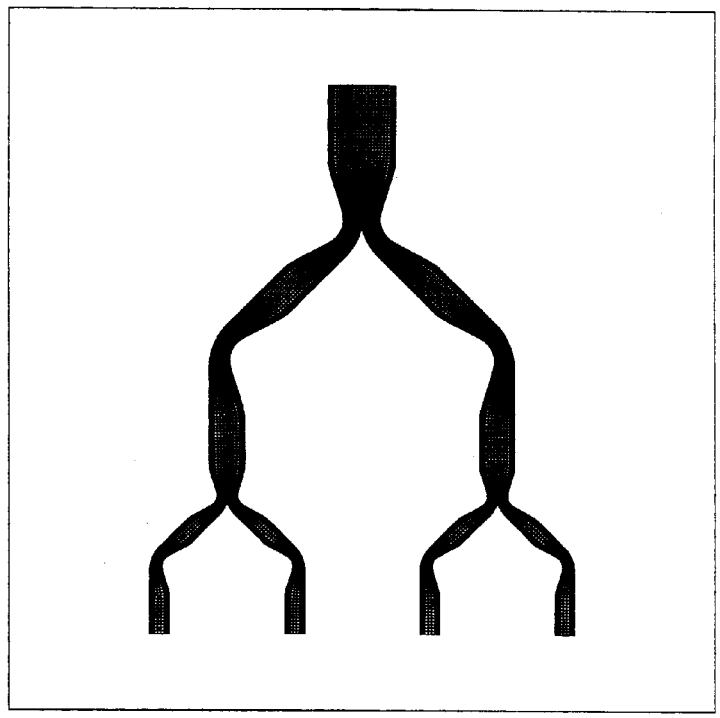
FIG. 15 is a plan view of an improved splitting device where the length of sample travel along any path through the branch network is the same such that sub-samples arrive simultaneously at all outlet ends.
Figure 16:
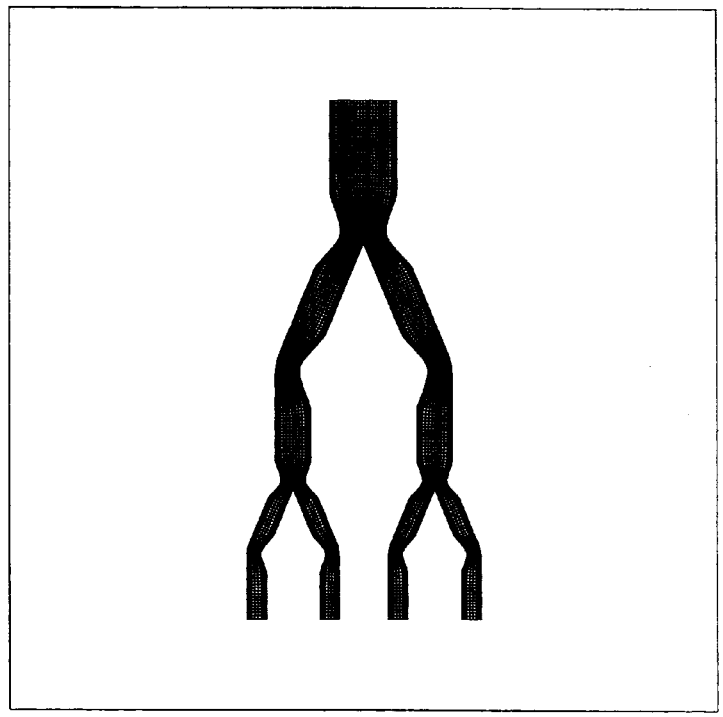
FIG. 16 is a plan view of an improved splitting device where the device may be operated to divide a sample into a plurality of sub-samples or to join several sub-samples into a single sample.

FIGS. 15 and 16 illustrate another embodiment of the present invention. These two devices enable splitting a single sample into any even number of smaller, but otherwise identical, sub-samples. Using these devices, a single sample can be routed to a collection of separation or processing channels each having the same or differing functions. Such multichannel processing is needed, for example, to identify the composition of an unknown sample that might contain a broad range of possible chemical or biological species. The sample splitting strategy of our invention is preferred to making separate injections into each of the processing channels because separate injections would require a multiplicity of injection channels, electrical connections, and electrical controls. In comparing FIGS. 15 and 16 it is apparent that the smaller splitting angle of FIG. 16 provides a more compact channel structure thereby conserving space on the substrate. A smaller splitting angle is also beneficial in reducing dispersion.

The branching devices shown in FIGS. 11 and 12 not only serve to divide a sample. Simply by transporting sub-samples in the reverse direction, these devices may also be used to join sub-samples in confluence at a single detector or other processing site. In the two illustrative geometries, the end-to-end paths through all branches are the same length, yielding simultaneous arrival of all sub-samples at the exit plane. However, subsample arrival times can be tailored to any desired pattern by varying the lengths of the linear segments joining the wyes and turns. For example, sequential arrivals might be advantageous in routing multiple sub-samples to a single detector. In this instance it is also likely that channel widths would remain the same at successive junctions. The same would also be true of switching junctions specifically designed to route an incoming sample into just one of the outgoing branches, depending on the pressures or electric potentials applied to each of the legs.

The tree like splitting or joining devices shown in FIG. 15 and 16 are each constructed by assembling only two basic building blocks. Each tree is constructed from a sequence of identical wye junctions, reduced in overall size by a factor of two at each successive level, joined by a short linear channel to matching turns that restore the direction of sample motion. Thus, only a few fundamental channel shapes are needed to construct a wide range of complex geometries. These building-block geometries can be scanned in from the figures presented here, digitized, and accurately scaled to the particular sizes needed in preparing lithographic masks for any microchannel device. Similarly, the total dispersion induced by any such composite device can be readily calculated from the known contributions of the fundamental turns and junctions.

Finally, the geometries of both the low-dispersion turns and junctions presented here are not readily discerned by experimental means. To obtain just a single optimized geometry requires several hundred realizations of sample transport through candidate turns or junctions, and each computational realization of a candidate geometry is equivalent to a single experiment. As a result, it is unlikely that geometries matching the dispersion performance of those described here could be obtained by experimental methods alone. In the course of designing just those geometries shown here, over 5000 such realizations were computed. As a result of this unique design process, the normalized variance, $L^*=(\sigma/\alpha)^2$, does not exceed 0.01 for any of the low-dispersion turns and junctions shown here. The largest value, $L^*=0.0071$, was produced by the low-dispersion 180 degree turn shown in FIG. 6. Other realizations, such as the 45 degree turn of FIG. 8 and the 22.5 degree junction of FIG. 12 produce much smaller normalized variance of only $L^*=0.0024$ and 0.0023, respectively. These levels of dispersion are, in all cases, at least 75 times smaller than that of the corresponding conventional turns and junctions. Moreover, in most cases the dispersion is reduced by more than a factor of one hundred.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A low-dispersion device for turning the direction of transport of a moving sample that comprises: a microchannel system comprising at least one turning channel having an inlet end and an outlet end, an inner wall and an outer wall, and an included turn angle, wherein the turning channel comprises contraction and expansion regions such that a portion of the turning channel is constricted to a width that is smaller than the widths of the inlet and outlet ends and wherein the turning channel has a cross-section that is rectangular, trapezoidal, or triangular.

2. The device of claim 1 wherein the contraction and expansion regions define inner and outer walls of the turning channel that are substantially equal in length.

3. The device of claim 1 wherein the turning channel has a depth that is substantially uniform.

4. The device of claim 1 wherein the turning channel has an included angle of greater than 10 degrees.

5. The device of claim 1 wherein the turning channel has an included angle equal to about 45 degrees.

6. The device of claim 1 wherein the turning channel has an included angle equal to about 90 degrees.

7. The device of claim 1 wherein the turning channel has an included angle equal to about 180 degrees.

8. The device of claim 1 wherein the constricted portion of the turning channel has a width that is between 20% and 80% of the width of the inlet end.

9. The device of claim 1 wherein the contraction and expansion regions have lengths that are between one and five times the width of the inlet end.

10. The device of claim 1 wherein the contraction and expansion regions extend into the turn.

11. The device of claim 1 wherein the angular span of the constricted portion of the turning channel is less than the included angle of the turn.

12. The device of claim 1 wherein the contraction and expansion regions and the constricted portion of the turning channel are configured such that sample motion through the turning channel produces a sample profile having a normalized variance, $L^*=(\sigma/\alpha)^2$ that is less than about 0.01, wherein $\sigma^2$ is the spatial variance of the sample profile at the outlet end of the turning channel and a is the width of the inlet end.

13. The device of claim 1 wherein a portion of the microchannel system comprises a separation matrix disposed therein.

14. The device of claim 1 further comprising at least two channel segments each defining a substantially linear path, wherein at least two linear channel segments are joined by a turning channel.

15. The device of claim 14 wherein the turning channel has an included angle that is greater than about 90 degrees.

16. The device of claim 14 wherein the turning channel has an included turn angle equal to about 180 degrees such that the final direction of motion of the moving sample is opposite to the initial direction.

17. The device of claim 14 wherein at least one linear channel segment comprises a separation matrix disposed therein.

18. A low-dispersion device for turning the direction of transport of a moving sample that comprises: a microchannel system comprising at least one turning channel having an inlet end and an outlet end, an inner wall and an outer wall, and an included turn angle, wherein the turning channel comprises contraction and expansion regions such that a portion of the turning channel is constricted to a width that is smaller than the widths of the inlet and the outlet ends, and wherein the contraction and expansion regions define inner and outer walls of the turning channel that are substantially equal in length.

19. A low-dispersion device for turning the direction of transport of a moving sample that comprises: a microchannel system comprising at least one turning channel having an inlet end and an outlet end, an inner wall and an outer wall, and an included turn angle, wherein the turning channel comprises contraction and expansion regions such that a portion of the turning channel is constricted to a width that is smaller than the widths of the inlet and the outlet ends, and wherein the outer wall of the turning channel comprises linear segments at the inlet and outlet ends joined by an arc of fixed radius spanning the included turn angle and wherein the inner wall of the turning channel is configured to form the contraction and expansion regions.

20. A low-dispersion device for dividing a sample that comprises: a microchannel system comprising at least one branching junction having one inlet end and at least two outlet ends, wherein the branching junction comprises contraction and expansion regions such that a portion of the branching junction is constricted to a width that is smaller than the width of at least one outlet end and wherein the branching junction has a cross-section that is rectangular, trapezoidal, or triangular.

21. The device of claim 20 wherein the branching junction has a depth that is substantially uniform.

22. The device of claim 20 wherein a portion of the branching junction is constricted to a width that is smaller than the width of at least one outlet end.

23. The device of claim 20 wherein the included angle between the inlet end and at least one outlet end is greater than 10 degrees.

24. The device of claim 20 wherein the included angle between the inlet end and at least one outlet end is about 90 degrees.

25. The device of claim 20 wherein the constricted portion of the branching junction has a width that is between 20% and 80% of the width of the outlet end.

26. The device of claim 20 and wherein the contraction and expansion regions have lengths that are between one and five times the width of the inlet end.

27. The device of claim 20 wherein the constricted portion and contraction and expansion regions are configured such that the sample motion through the branching junction produces a sample profile having a normalized variance, $L^*=(\sigma/\alpha)^2$, that is less than about 0.01, wherein $\sigma^2$ is the spatial variance of the sample profile at one or more outlet ends and $\alpha$ is the width of the inlet end.

28. The device of claim 20 wherein a portion of the microchannel system comprises a separation matrix disposed therein.

29. A low-dispersion device for dividing a sample that comprises: a microchannel system comprising at least one branching junction having one inlet end and at least two outlet ends, wherein the branching junction comprises contraction and expansion regions such that a portion of the branching junction is constricted to a width that is smaller than the width of at least one outlet end and wherein an included turn angle between the inlet end and at least one outlet end is about 22.5 degrees.

30. A low-dispersion device for dividing a sample that comprises: a microchannel system comprising at least one branching junction having one inlet end and at least two outlet ends, wherein the branching junction comprises contraction and expansion regions such that a portion of the branching junction is constricted to a width that is smaller than the width of at least one outlet end and wherein an included turn angle between the inlet end and at least one outlet end is about 45 degrees.

31. A low-dispersion device for dividing a sample that comprises: a microchannel system comprising at least one branching junction having one inlet end and at least two outlet ends, wherein the branching junction comprises contraction and expansion regions such that a portion of the branching junction is constricted to a width that is smaller than the width of at least one outlet end, and wherein the joining of adjacent junction walls interior of the outlet ends defines a cusp.

32. A low-dispersion device for dividing a sample that comprises: a microchannel system comprising at least one branching junction having one inlet end and at least two outlet ends, wherein the branching junction comprises contraction and expansion regions such that a portion of the branching junction is constricted to a width that is smaller than the width of at least one outlet end, and wherein the contraction and expansion regions of the branching junction define a first distance of travel along one outer junction wall and a second distance of travel starting at the center of the inlet end and proceeding along the junction wall interior of one outlet end, and wherein the first and second distance of travel are substantially equal.

33. A low-dispersion device for dividing a sample that comprises: a microchannel system comprising first, second, and third branching junctions and at least two turning channels wherein each branching junction comprises one inlet end and at least two outlet ends, and the outlet ends of the first branching junction are joined by turning channels to the inlet ends of the second and third branching junctions and at least one of said first, second and third branching junctions comprises contraction and expansion regions such that a portion of the branching junction is constricted to a width that is smaller than the width of at least one of its outlet ends.

34. The device of claim 33 wherein the branching junctions and turning channels comprise a separation matrix disposed therein.

35. A low-dispersion device for joining two or more samples that comprises: a microchannel system comprising at least one confluence junction having at least two inlet ends and one outlet end, wherein the confluence junction comprises contraction and expansion regions such that a portion of the confluence junction is constricted to a width that is smaller than the width of at least one inlet end and wherein the confluence junction has a cross-section that is rectangular, trapezoidal, or triangular.

36. An apparatus for analyzing chemical or biological samples containing a plurality of species that comprises:
   a substrate fabricated to define a microchannel system disposed therein, the microchannel system comprising at least one turning channel having an inlet and an outlet end, wherein the turning channel comprises contraction and expansion regions such that a portion of the turning channel is constricted to a width that is smaller than the width of the inlet and outlet ends, and wherein the turning channel has a cross-section that is rectangular, trapezoidal, or triangular;
   means for introducing a sample into the microchannel system;
   means for separating the sample into two or more components; and
   means for detecting the two or more different components.

37. The apparatus of claim 36 wherein the separation means comprises applied pressures used to create a pressure gradient along some portion of the microchannel system in order to cause fluid motion and species separation by chromatography.

38. The apparatus of claim 36 wherein at least a portion of the microchannel system comprises a separation matrix disposed therein.

39. The apparatus of claim 36 wherein the substrate material is selected from the group consisting of silicon, silicon compounds, silicone, glass, and polymers.

40. The apparatus of claim 36 wherein in the microchannel system is embossed into the substrate.

41. The apparatus of claim 36 wherein the microchannel system is etched into the substrate.

42. The apparatus of claim 36 wherein the substrate is injection molded to form the microchannel system.

43. An apparatus for analyzing chemical or biological samples containing a plurality of species that comprises:
   a substrate fabricated to define a microchannel system disposed therein, the microchannel system comprising at least one turning channel having an inlet and an outlet end, wherein the turning channel comprises contraction and expansion regions such that a portion of the turning channel is constricted to a width that is smaller than the widths of the inlet and outlet ends;
   means for introducing a sample into the microchannel system;
   means for separating the sample into two or more components;
   and means for detecting the two or more different components, wherein the separation means comprises electrodes and an electric controller used to create a voltage gradient along some portion of the microchannel system in order to cause species separation by electrophoresis.

44. An apparatus for analyzing chemical or biological samples containing a plurality of species that comprises:
   a substrate fabricated to define a microchannel system disposed therein, the microchannel system comprising at least one turning channel having an inlet and an outlet end, wherein the turning channel comprises contraction and expansion regions such that a portion of the turning channel is constricted to a width that is smaller than the widths of the inlet and outlet ends and wherein the turning channel has a cross-section that is rectangular, trapezoidal, or triangular;

means for introducing a sample into the microchannel system;

means for separating the sample into two or more components; and means for detecting the two or more different components, wherein the separation means comprises electrodes and an electric controller used to create a voltage gradient along some portion of the microchannel system in order to cause electroosmotic flow and species separation by chromatography.

45. A method for analyzing chemical and biological samples by separating a sample into two or more component species wherein the method comprises the steps of:

providing an apparatus comprising a microchannel system, the microchannel system comprising at least one turning channel having an inlet end and an outlet end, wherein the turning channel comprises contraction and expansion regions such that a portion of the turning channel is constricted to a width that is smaller than the widths of the inlet and outlet ends, and wherein the turning channel has a cross-section that is rectangular, trapezoidal, or triangular;

introducing a sample into the microchannel system;

separating the sample into two or more components; and detecting the two or more different components.

46. The method of claim 45 wherein the step of separating the sample causes the sample to travel through the microchannel system and turning channel to form one or more discrete bands and whereby the bands exhibit negligible dispersion as they travel through the turning channel and wherein the turning channel has a cross-section that is rectangular.

47. A low-dispersion microchannel device for turning the direction of transport of a moving sample comprising: a turning channel having an inlet end and an outlet end, wherein the turning channel comprises a region in which the cross-sectional area is smaller than that of the inlet end and wherein the turning channel has a cross-section that is rectangular, trapezoidal, or triangular.

48. A low-dispersion device for turning the direction of transport of a moving sample that comprises: a microchannel system comprising at least one turning channel having an inlet end and an outlet end, an inner wall and an outer wall, and an included turn angle, wherein the turning channel comprises contraction and expansion regions such that a portion of the turning channel is constricted to a width that is smaller than the widths of the inlet and the outlet ends, and wherein the length of the inner wall along the contraction region is longer than the length of the outer wall along the contraction region.

49. A low-dispersion device for turning the direction of transport of a moving sample that comprises: a microchannel system comprising at least one turning channel having an inlet end and an outlet end, an inner wall and an outer wall, and an included turn angle, wherein the turning channel comprises contraction and expansion regions such that a portion of the turning channel is constricted to a width that is smaller than the widths of the inlet and the outlet ends, and wherein the length of the inner wall along the expansion region is longer than the length of the outer wall along the expansion region.

50. A low-dispersion device for turning the direction of transport of a moving sample that comprises: a microchannel system comprising at least one turning channel having an inlet end and an outlet end, an inner wall and an outer wall, and an included turn angle, wherein the inner and outer walls at the inlet end are substantially parallel and define a centerline of the inlet end that is midway between and parallel to said inner and outer walls at the inlet end, wherein the turning channel comprises contraction and expansion regions such that a portion of the turning channel is constricted to a width that is smaller than the widths of the inlet and the outlet ends, and wherein the contraction region is asymmetric with respect to the centerline of the inlet end.

51. The apparatus of claim 50 wherein the distance between the inner wall and the centerline of the inlet end is less than the distance between said centerline of the inlet end and the outer wall for at least some portion of the contraction region.

52. The apparatus of claim 50 wherein the inner wall of the turning channel crosses the centerline of the inlet end.

53. A low-dispersion device for turning the direction of transport of a moving sample that comprises: a microchannel system comprising at least one turning channel having an inlet end and an outlet end, an inner wall and an outer wall, and an included turn angle, wherein the inner and outer walls at the outlet end are substantially parallel and define a centerline of the outlet end that is midway between and parallel to said inner and outer walls at the outlet end, wherein the turning channel comprises contraction and expansion regions such that a portion of the turning channel is constricted to a width that is smaller than the widths of the inlet and the outlet ends, and wherein the expansion region is asymmetric with respect to the centerline of the outlet end.

54. The apparatus of claim 53 wherein the distance between the inner wall and the centerline of the outlet end is less than the distance between said centerline of the outlet end and the outer wall for at least some portion of the expansion region.

55. The apparatus of claim 53 wherein the inner wall of the turning channel crosses the centerline of the outlet end.

56. A low-dispersion device for turning the direction of transport of a moving sample that comprises: a microchannel system comprising at least one turning channel having an inlet end, an inner wall and an outer wall, and an included turn angle, wherein the turning channel comprises contraction and expansion regions such that a portion of the turning channel is constricted to a width that is smaller than the widths of the inlet and the outlet ends, and wherein the inner wall defines a path having at least one inflection point in the contraction region and having at least one inflection point in the expansion region, and expansion regions.

57. A low-dispersion device for dividing a sample that comprises: a planar substrate patterned to define a microchannel system comprising at least one branching junction having one inlet end and at least two outlet ends, wherein the sum of the widths of the two outlet ends is substantially equal to the width of the inlet end, and wherein the branching junction comprises contraction and expansion regions such that a portion of the branching junction is constricted to a width that is smaller than the width of at least one outlet end.

58. The apparatus of claim 57 wherein the planar substrate is patterned to define the microchannel system by embossing, etching or molding.

59. The apparatus of claim 57 wherein the width of each of said two outlet ends is substantially equal to twice the width of said inlet end.

60. A low-dispersion device for joining two or more samples that comprises: a planar substrate patterned to define a microchannel system comprising at least one confluence junction having at least two inlet ends and one outlet end, wherein the confluence junction comprises contraction and expansion regions such that a portion of the confluence junction is constricted to a width that is smaller than the width of at least one inlet end.

61. The apparatus of claim 60 wherein the planar substrate is pattered to define the microchannel system by embossing, etching or molding.

62. The apparatus of claim 60 having two inlet ends and one outlet ends wherein the sum of the widths of the two inlet ends is substantially equal to the width of the outlet end.

63. The apparatus of claim 62 wherein the width of each of said two inlet ends is substantially equal to twice the width of said outlet end.

* * * * *